United States Patent
Cantwell et al.

(10) Patent No.: US 11,426,109 B2
(45) Date of Patent: *Aug. 30, 2022

(54) NERVE MONITORING AND/OR STIMULATION ELECTRODE ASSEMBLIES

(71) Applicant: Medtronic Xomed, Inc., Jacksonville, FL (US)

(72) Inventors: Matthew L. Cantwell, Orange Circle, FL (US); David C. Hacker, Jacksonville, FL (US); John R. Prisco, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 54 days.

This patent is subject to a terminal disclaimer.

(21) Appl. No.: 16/929,886

(22) Filed: Jul. 15, 2020

(65) Prior Publication Data

US 2020/0345257 A1 Nov. 5, 2020

Related U.S. Application Data

(63) Continuation of application No. 15/907,980, filed on Feb. 28, 2018, now Pat. No. 10,729,342.

(51) Int. Cl.
*A61N 1/05* (2006.01)
*A61B 5/24* (2021.01)
*A61B 5/00* (2006.01)

(52) U.S. Cl.
CPC .............. *A61B 5/24* (2021.01); *A61B 5/4029* (2013.01); *A61B 5/4041* (2013.01);
(Continued)

(58) Field of Classification Search
CPC ... A61B 5/4029; A61B 5/4041; A61B 5/6848; A61B 5/687; A61B 5/6884; A61B 2562/0209; A61N 1/0556
See application file for complete search history.

(56) References Cited

U.S. PATENT DOCUMENTS

| | | | |
|---|---|---|---|
| 4,040,697 | A | 8/1977 | Ramsay et al. |
| 4,080,961 | A | 3/1978 | Eaton |

(Continued)

FOREIGN PATENT DOCUMENTS

| | | |
|---|---|---|
| FR | 2372636 | 6/1978 |
| GB | 2351911 | 1/2001 |

(Continued)

OTHER PUBLICATIONS

Chiang et al., "Comparison of EMG signals recorded by surface electrodes on endotracheal tube and thyroid cartilage during monitored thyroidectomy", KJMS (May 15, 2017) 33, 503-509.
(Continued)

*Primary Examiner* — Paula J Stice
(74) *Attorney, Agent, or Firm* — Dicke, Billig & Czaja, PLLC

(57) ABSTRACT

Stimulation and recording electrode assemblies that are particularly useful for Automatic Period Stimulation (APS). Such embodiments are compatible with nerve monitoring systems to provide continuous stimulation of a nerve during surgery. Certain embodiments include an electrode assembly having cuff including a body and two ears extending from the body. Within the body, at least one electrode is supported and connected to a lead wire assembly. The ears can be brought together to enlarge a gap in the body so that the electrode assembly can be fixated around a nerve. Other embodiments include an electrode assembly including first and second needle electrodes that each have a tip. A body is provided to interconnect the needle electrodes and can be manipulated to move the tips either toward or away from one another. Disclosed embodiments provide nerve monitoring and stimulation in cases where the nerve is only partially dissected.

18 Claims, 9 Drawing Sheets

(52) U.S. Cl.
CPC .......... *A61B 5/6848* (2013.01); *A61B 5/6877* (2013.01); *A61B 5/6884* (2013.01); *A61N 1/0556* (2013.01); *A61B 2562/0209* (2013.01)

(56) References Cited

U.S. PATENT DOCUMENTS

| | | | |
|---|---|---|---|
| 4,177,818 | A | 12/1979 | De Pedro |
| 4,178,052 | A | 12/1979 | Ekbom et al. |
| 4,254,764 | A | 3/1981 | Neward |
| 4,303,293 | A | 12/1981 | Grunwald |
| 4,385,793 | A | 5/1983 | Koford et al. |
| 4,649,923 | A | 3/1987 | Hoffman |
| 4,777,954 | A | 10/1988 | Keusch et al. |
| 4,827,939 | A | 5/1989 | Cartmell et al. |
| 5,375,594 | A | 12/1994 | Cueva |
| 5,421,748 | A * | 6/1995 | Mouissie ............... H01R 13/41 439/740 |
| 5,931,861 | A | 8/1999 | Werner et al. |
| 6,122,554 | A | 9/2000 | Coral et al. |
| 6,135,953 | A | 10/2000 | Carim |
| 6,308,105 | B1 * | 10/2001 | Duysens ............... A61N 1/0551 607/116 |
| 6,343,233 | B1 | 1/2002 | Werner et al. |
| 7,627,384 | B2 | 12/2009 | Ayal et al. |
| 7,797,058 | B2 | 9/2010 | Mrva et al. |
| 8,868,211 | B2 | 10/2014 | Durand et al. |
| 9,114,250 | B2 | 8/2015 | True et al. |
| 9,226,680 | B1 | 1/2016 | Kendricks |
| 9,227,053 | B2 | 1/2016 | Bonde et al. |
| 9,283,379 | B2 | 3/2016 | True et al. |
| 10,729,342 | B2 | 8/2020 | Cantwell et al. |
| 10,994,130 | B2 | 5/2021 | Clements et al. |
| 2004/0176831 | A1 | 9/2004 | Gliner et al. |
| 2010/0145221 | A1 * | 6/2010 | Brunnett ............... A61B 5/4041 600/554 |
| 2010/0145222 | A1 | 6/2010 | Brunnett et al. |
| 2010/0168831 | A1 | 7/2010 | Korivi et al. |
| 2011/0237921 | A1 | 9/2011 | Askin, III et al. |
| 2013/0338749 | A1 | 12/2013 | Brunnett et al. |
| 2014/0142410 | A1 | 5/2014 | Erb et al. |
| 2016/0058380 | A1 | 3/2016 | Lee et al. |
| 2016/0120475 | A1 | 5/2016 | Cha et al. |
| 2017/0197076 | A1 | 7/2017 | Faltys et al. |
| 2017/0266436 | A1 | 9/2017 | Suwito et al. |
| 2019/0059813 | A1 | 2/2019 | McFarlin et al. |
| 2019/0104956 | A1 | 4/2019 | Cantwell et al. |
| 2019/0104995 | A1 | 4/2019 | Cantwell et al. |

FOREIGN PATENT DOCUMENTS

| | | |
|---|---|---|
| KR | 2012-0096675 | 8/2012 |
| WO | 94/22365 | 10/1994 |
| WO | 2009135138 | 11/2009 |
| WO | 2014055393 | 4/2014 |
| WO | 2018045056 | 3/2018 |

OTHER PUBLICATIONS

APS Electrode YouTube video, https://www.youtube.com/watch?v=LUomWViTnVA, published on Dec. 10, 2014.

PCT Partial Search Report dated Feb. 21, 2019 for PCT/US2018/065326 (14 pages).

C.F. Sinclair et al., "Contralateral R1 and R2 Components of the Laryngeal Adductor Reflex in Humans Under General Anesthesia", The Laryngoscope, 127 12, E443-E448 (2017).

PCT Search Report and Written Opinion dated Dec. 20, 2018 for PCT/US2018/054530 (13 pages).

G. Dionigi et al., "Continuous Intraoperative Neuromonitoring (C-IONM) Technique with the Automatic Periodic Stimulating (APS) Acessory for Conventional and Endoscopic Thyroid Surgery", General Surgery, Surgical Technology International XXVI, May 26, 2015, pp. 101-114.

PCT Search Report and Written Opinion dated Apr. 5, 2019 for PCT/US2018/065326 (18 pages).

Hoffer et al., Ch. 5, "How to Use Nerve Cuffs to Stimulate, Record or Modulate Neural Activity," Neural Prostheses for Restoration of Sensory and Motor Function, CRC Press, pp. 139-175 (2001).

San Martin, "Protocol for Neurophysiological Studies of the Superior and Recurrent Laryngeal Nerves and of the Cricothyroid and Thryoarytenoid Muscles," J. Otolaryngology-ENT Research, vol. 6, Issue 1, pp. 1-10 (Jan. 30, 2017).

* cited by examiner

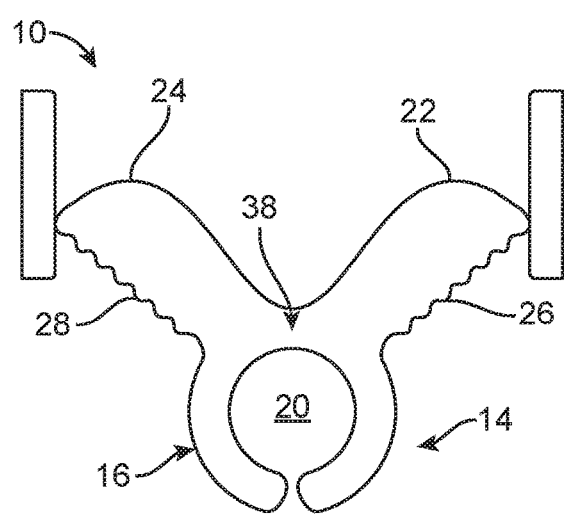
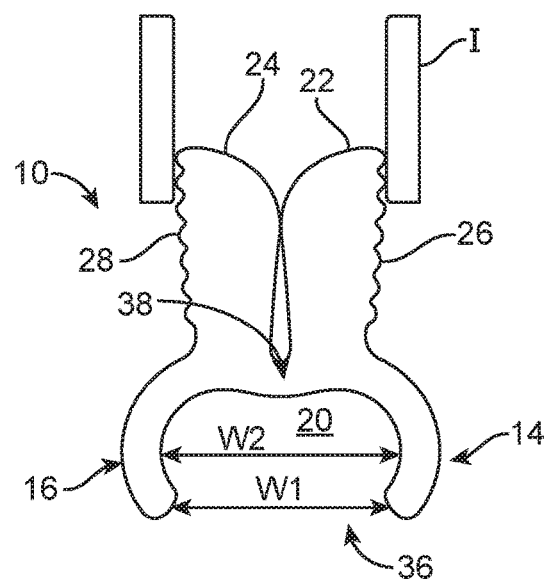
FIG. 3A    FIG. 3B
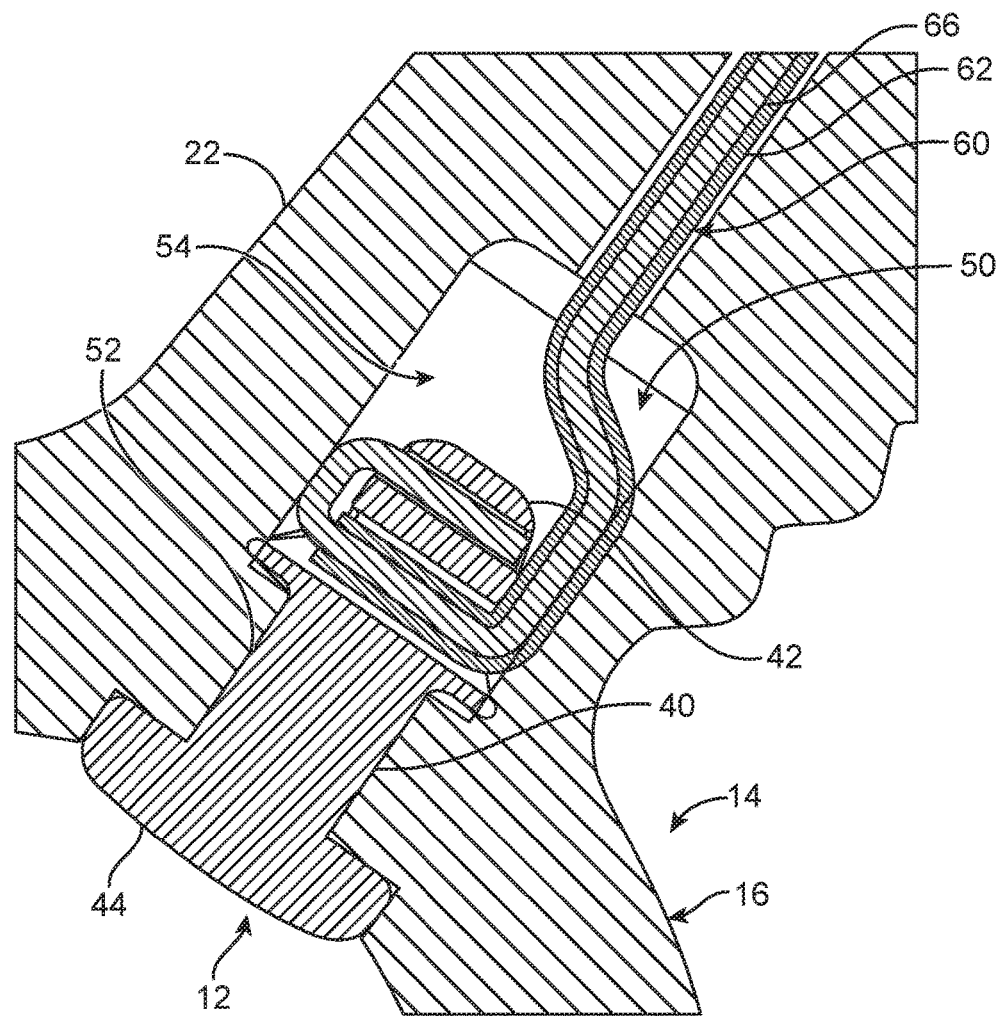
FIG. 4

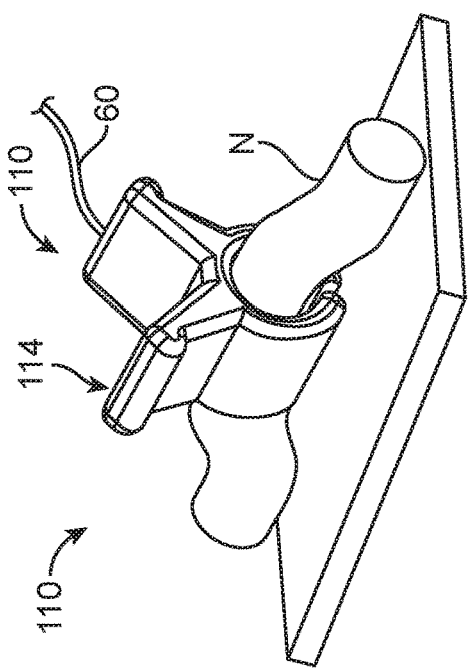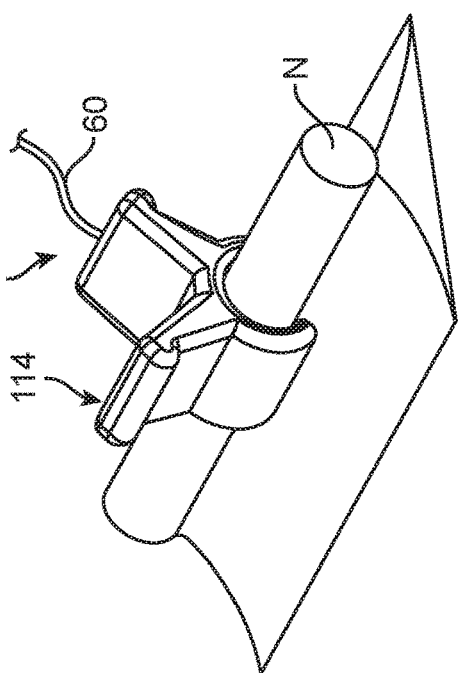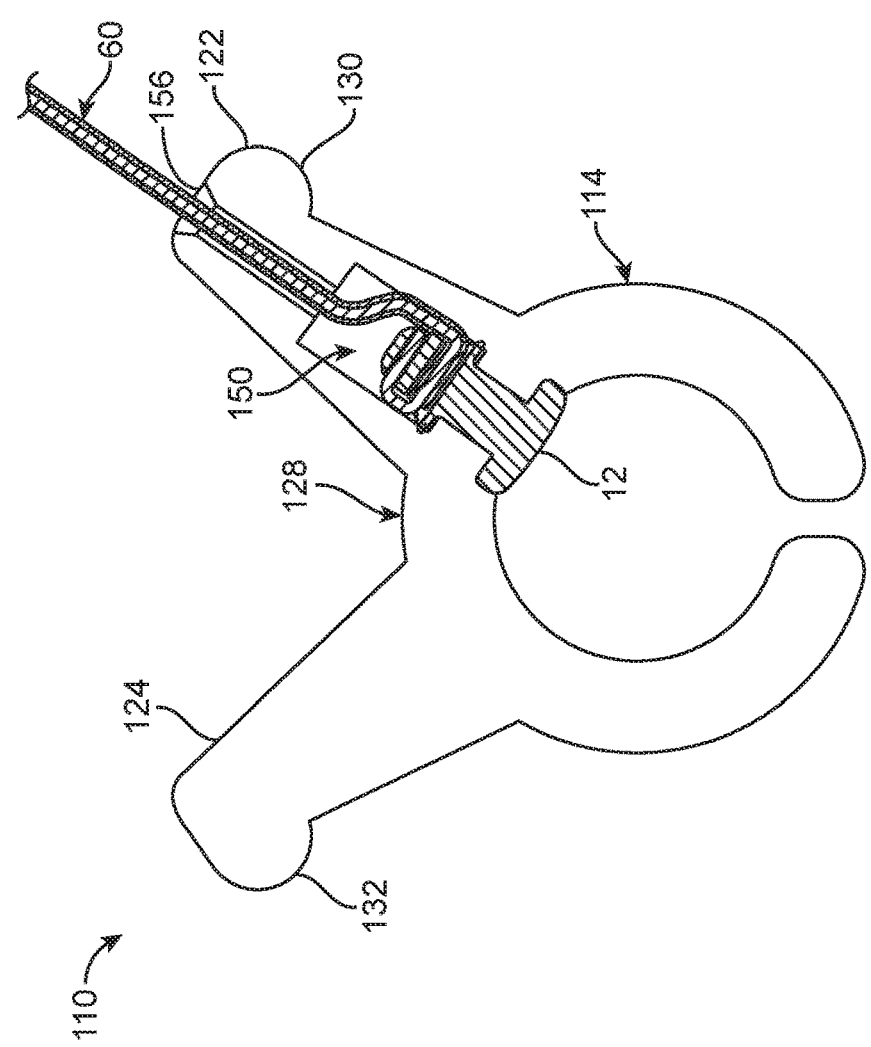

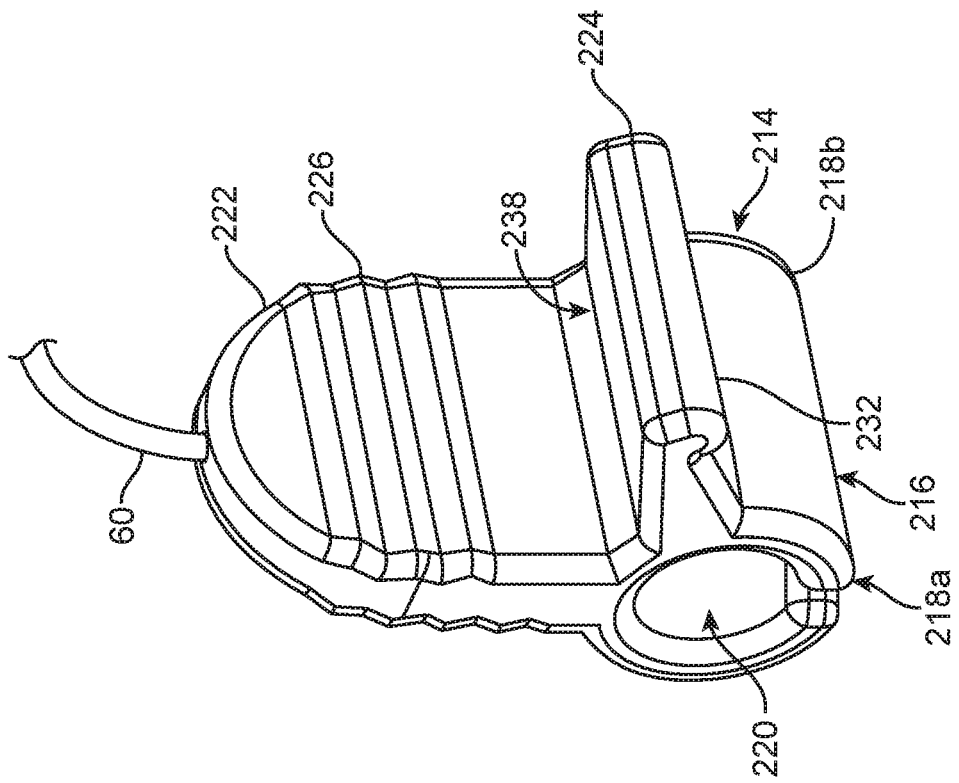
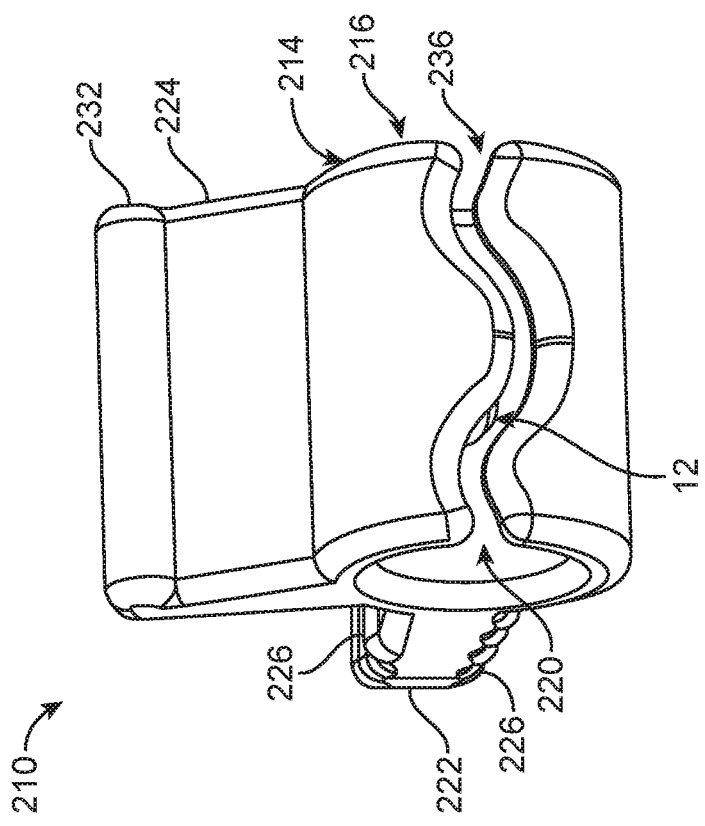
FIG. 11B
FIG. 11A

NERVE MONITORING AND/OR STIMULATION ELECTRODE ASSEMBLIES

CROSS-REFERENCE TO RELATED APPLICATIONS

This application is a continuation of U.S. application Ser. No. 15/907,980, filed Feb. 28, 2018, now U.S. Pat. No. 10,729,342, entitled "NERVE MONITORING AND/OR STIMULATION ELECTRODE ASSEMBLIES," the contents of which are incorporated herein by reference.

BACKGROUND

Nerve monitoring is used in surgical procedures where nerves are at risk. With some systems, a monitor and hand-held stimulator probe provides intermittent stimulation only when the surgeon probes the nerve. Nerves can be at risk, however, in between stimulations due to surgical incision "blind" trauma caused by manipulation and stretching during tumor removal, and cumulative trauma or damage that may result in neuropraxla. Automatic Periodic Stimulation (APS), however, provides Continuous Intraoperative Nerve Monitoring (C-IONM). Intraoperative Nerve Integrity Monitor (NIM) systems enable surgeons to identify, confirm, and monitor motor nerve function to help reduce the risk of nerve damage during various procedures including ENT and general surgeries.

One such system is Medtronic's NIM® Nerve Monitoring System, which includes an electromyographic (EMG) monitor for intraoperative use during various surgeries in which a nerve may be at risk due to unintentional manipulation. MM nerve monitoring probes having electrodes are placed in the appropriate muscle locations in the patient for the procedure being performed. These electrodes are connected to the NIM Nerve Monitoring System, which continuously monitors EMG activity from muscles innervated by the affected nerve. When a particular nerve has been activated or stimulated, the NIM System warns the surgeon and operating room staff, providing both visual alerts on the color touchscreen monitor and audio feedback to help minimize trauma to the nerve.

Surgeons can use monopolar and bipolar stimulating probes and dissection instruments with the NIM® Nerve Monitoring System to assist in early nerve identification and confirmation. These tools may be used to locate, identify, and map the particular nerve and branches, as well as verify nerve function and integrity to help surgeons perform critical procedures while preserving nerve function and improving patient safety.

The present disclosure provides improvements associated with the related art.

SUMMARY

Aspects of the disclosure are related to stimulation and recording electrode assemblies that are particularly useful for Continuous Intraoperative Nerve Monitoring (C-IONM), Automatic Periodic Stimulation (APS) or Therapeutic Stimulation. Such embodiments are compatible with nerve monitoring systems to provide continuous stimulation of a nerve during surgery in which nerves are at risk. Examples of surgeries in which the disclosed embodiments are particularly useful include facial nerve, parotidectomy, thyroidectomy, endoscopic and lateral skull base surgeries.

Disclosed embodiments include an electrode assembly having an electrode supported by and positioned within a deformable cuff. In one illustrative embodiment, the cuff includes a body having a first end, a second end, and defining a first channel configured to receive the nerve. The cuff further includes first and second ears extending radially outwardly from the body. A second channel is formed in the first ear for housing and supporting an electrode. The body can additionally maintain a second electrode for bipolar applications. The body defines a gap and a width of the gap is variable and configured to support a degree fixation to the nerve that is less than 360 degrees. In other words, embodiments of the disclosure are suitable for use with partially-dissected nerves. A lead wire assembly is interconnected to each electrode and extends through the second channel. In use, the ears can be squeezed together to allow an operator to expand the gap in the cuff for placing the cuff at least partially around a nerve. In this way, the electrode assembly is maintained in position, wrapped around the nerve.

Other various disclosed embodiments include a self-retaining needle electrode assembly, which also allows minimal nerve dissection to place in position. The electrode assembly can include first and second needle electrodes; wherein the first needle electrode includes a first tip and the second needle electrode includes a second tip. The electrode assembly further includes a body interconnecting the first and second needle electrodes having a first end, a second end, a first side portion and a second side portion. The body includes a resilient hinge segment interconnecting the first and second side portions. The body has a natural arrangement and the body also has an expanded arrangement in which the first and second side portions are drawn together at the second end such that the first and second tips are positioned further away from each other as compared to the natural arrangement. A lead wire assembly interconnected to the first and second electrodes is also provided. The self-retaining needle electrode assembly may be particularly useful, for example, for stimulating and recording from muscle (e.g., cricothyroid) in thyroid procedures.

The disclosed embodiments provide for continuous intraoperative monitoring and/or therapeutic stimulation in current and new procedures without extra dissection or necessarily wrapping of the electrode assembly around the entirety of the respective nerve. Various disclosed embodiments are configured for partially-dissected nerves in which less than an entirely (e.g., 50%) of the circumference of the nerve is exposed. For many procedures the procedure itself requires 50% or more of nerve dissection, therefore, no additional dissection is often required to place the disclosed electrode assemblies in position for use.

BRIEF DESCRIPTION OF THE DRAWINGS

FIG. 3A is a front view of the electrode assembly of FIG. 1 in a natural arrangement.

FIG. 3B is a front view of the electrode assembly in an expanded arrangement.

FIG. 4 is a partial, enlarged, cross-sectional view of the electrode assembly of FIG. 1 showing an electrode and lead wire assembly.

FIG. 8 is a cross-sectional view of an alternate electrode assembly.

FIG. 9 is a perspective view of the electrode assembly of FIG. 8 placed on a dissected nerve.

FIG. 10 is a perspective view of the electrode assembly of FIGS. 8-9 placed on a partially dissected nerve.

FIG. 11A is a bottom view of an alternate electrode assembly.

FIG. 11B is a perspective view of the alternate electrode assembly of FIG. 11A.

DETAILED DESCRIPTION

Figures 1, 2:
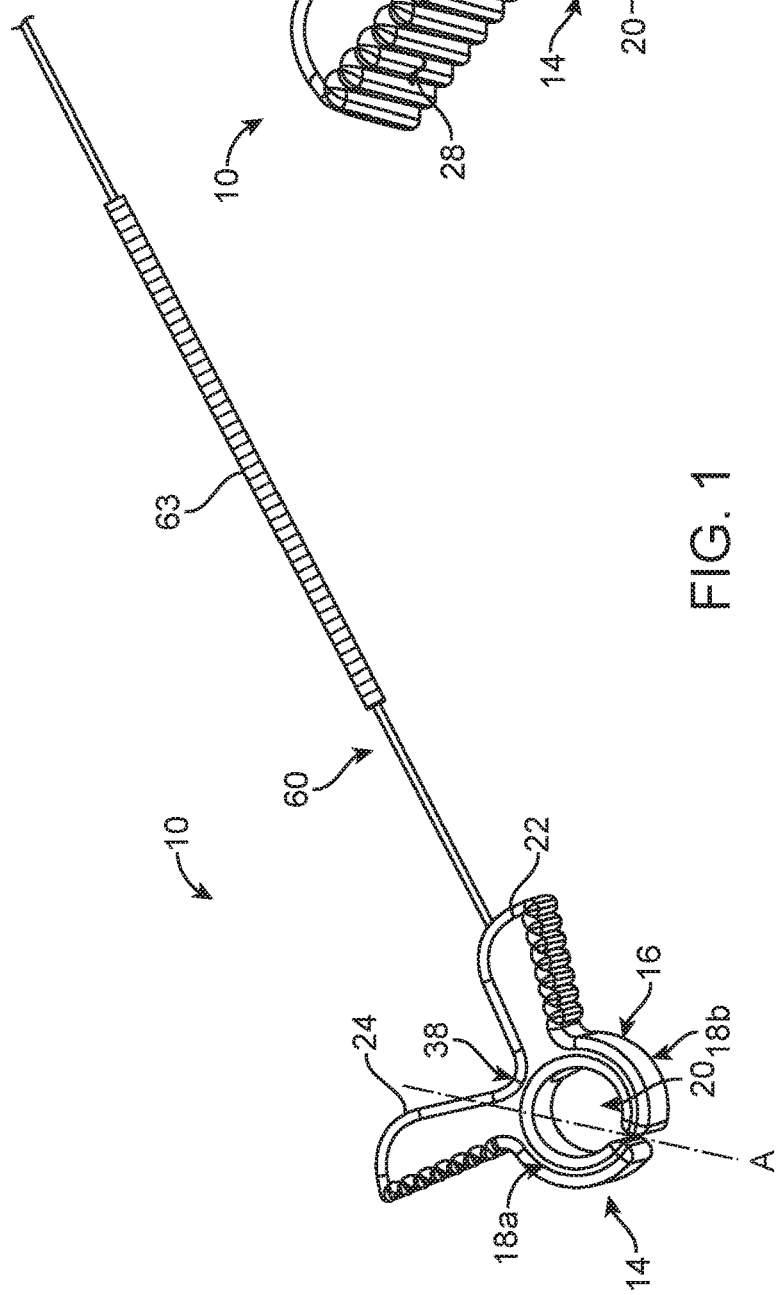
FIG. 1 is a perspective view of one embodiment of an electrode assembly.
FIG. 2 is a partial, enlarged view of the electrode assembly of FIG. 1.

Nerve monitoring is used in surgical procedures where nerves are at risk. A monitor and hand-held stimulator probe having an electrode provides intermittent stimulation only when the surgeon probes the nerve. Nerves can be at risk, however, in between stimulations due to surgical incision "blind" trauma caused by manipulation and stretching during tumor removal, and cumulative trauma or damage that may result in neuropraxia. Automatic Periodic Stimulation (APS), however, provides Continuous Intraoperative Nerve Monitoring (C-IONM). The electrode provides continuous, periodic stimulation of nerves used for trending amplitude and latency in real-time which includes adjustable alarm limits for significant baseline changes. This early warning helps alert the surgeon to stop surgical trauma as most injury is immediacy reversible but can become permanent if prolonged.

Aspects of the disclosure relate to stimulation and recording electrode assemblies that are particularly useful with APS. Such embodiments are compatible with nerve monitoring systems to provide continuous nerve stimulation during a surgical procedure. Two such compatible nerve monitoring systems include NIM-Response® 3.0 and NIM-Neuro® 3.0 nerve monitoring systems both available from Medtronic, Inc. of Minneapolis, Minn. The disclosed electrode assemblies are particularly useful for monitoring a facial nerve at a main trunk in head and neck procedures, as well as the facial nerve in Lateral Skull Base procedure (LSB) procedures. The electrode can be used for short procedures less than 24 hours or implanted in the patient longer than 24 hours. The electrode surface maybe coated to deliver a drug during contact or enhanced treatment such as through electro-paresis. The use of the disclosed embodiments, however, is not intended to be limited to those specific procedures. For example, the disclosed embodiments are also envisioned to be useful for stimulation therapy procedures. In one illustrative example, therapy can be achieved via electrical stimulation applied to a nerve at approximately 20 Hz stimulation rate.

One example embodiment of an electrode assembly 10 is illustrated in FIGS. 1-7. The electrode assembly 10 includes an evoked potential monitoring electrode 12 supported by and positioned within a cuff 14 including a body 16 having two parallel ends 18a, 18b. The body 16 further defines a channel 20 in which a nerve can be positioned. As shown, the body 16 can have a semi-circular cross-section (generally C-shaped) at both of the first and second ends 18a, 18b and/or throughout the body along the channel 20. Extending radially from the body are two ears or tabs 22, 24. In some embodiments, each ear 22, 24 can include a textured surface 26, 28 (e.g., ridges), which may assist in gripping the ear 22, 24 with a surgical instrument that may be tongs, for example (schematically depicted in FIGS. 3A-3B). As illustrated in FIGS. 3A-3B, the cuff 14 includes open and closed positions in which a width W1 of a gap 36 formed by the body 16 and also a width W2 of the channel 20 of the body 16 are varied via flexing of the cuff 14 at a hinge segment 38. The ears 22, 24 can be squeezed or moved together with the surgical instrument so that a hinge segment 38 of the body 16, positioned between the ears 22, 24, flexes and extends the width W1 of the gap 36 and the width W2 of the channel 20 such that tissue and/or a nerve can be scooped up or otherwise positioned within the channel 20 of the body 16. Once the instrument releases the ears 22, 24, due to the resilient nature of the body 16, the cuff 14 transitions back to the position of FIG. 3A in which the gap 36 has a reduced width W1 and the channel 20 has a reduced width W2 as compared to FIG. 3B. Suitable materials for the cuff 14 include, but are not limited to NuSil MED-4980 silicone rubber available from Nusil Technology LLC of Carpinteria, Calif., NuSil MED4980 silicone rubber with 25% NuSil MED2-4900 (both available from Nusil Technology LLC) and optional 2% colorant, C-Flex® TPE available from Holland Applied Technologies, Inc. of Burr Ridge, Ill., R70-095-000 Shore 65A, or similar elastomeric material.

In one embodiment, the gap 36 is positioned opposite (approximately 180 degrees) from the hinge segment 38. In some embodiments, the gap 36 is positioned at a circumferential distance from each ear 22, 24 and that distance is equal at both the first and second ends 18a, 18b of the body 16. The gap 36 can be linear, extending parallel with respect to a central axis A of the channel 20, from the first end 18a to the second end 18b or otherwise configured and provides for continuous intraoperative monitoring and/or therapeutic stimulation in current and new procedures that place nerves at risk without extra dissection or necessarily wrapping of the electrode assembly 10 substantially around an entire circumference (i.e. 360 degrees) of the respective nerve (as would require full dissection of the nerve). Various disclosed embodiments, are configured for partially-dissected nerves in which at least about 50% or more of the circumference of the nerve is exposed. Although the present embodiments can be used with nerves that are fully dissected in which 100% of the circumference of the nerve is exposed, any level of dissection that is greater than about 50% of the circumference is suitable. For many procedures the procedure itself requires this level of nerve dissection, therefore, no additional dissection is often required to place the present electrode assemblies in position for use. In various embodiments, the body 16 is configured to interface with nerves within the range of about 1 to about 4 mm. Therefore, in such embodiments, the width W2 of the channel 20 is in the range of about 1 mm to about 4 mm when secured around a nerve. One or more elements of the electrode assembly 10 can optionally include a pigment to provide chromatic differentiation between various body sizes and/or to differential the electrode assembly from the patient anatomy.

As is perhaps best shown in FIG. 4, the electrode 12 can be supported within a channel 50 formed within one ear 22. The channel 50 can have a variety of configurations. One example configuration includes a first portion 52 for receiving and retaining an axle 40 of the electrode 12. The first portion 52 is connected to a second portion 54, which receives a top 42 of the electrode 12 and at least a portion of a lead wire assembly 60. As will be discussed in more detail below, the lead wire assembly 60 includes at least one insulating jacket 62 positioned around a wire core 66.

The electrode 12 can be used as recording and stimulating electrode as well as therapeutic stimulating electrode. In some embodiments, as further disclosed below with respect to FIGS. 12A-12B, two electrodes can be provided to provide bipolar stimulation or recording and is configured to communicate electrical stimulus to tissues and thus must provide the appropriate surface area for contacting tissue for the current density. The material in which the electrode 12 is formed or surface treatment (not shown) provided on the electrode 12 at a base 44 (or interface at which the electrode 12 contacts the nerve) can be selected to enhance the bioelectric interface to tissue via selection of such preferred base metals, sintering to increase surface area, or plaiting. Suitable material examples for the electrode 12 at the interface or base 44 include stainless steel, copper, gold, iridium, palladium, platinum, rubidium, ruthenium, silver, conductive plastics or inks. Conductive plastics or inks can be used on the surface of the top 42 or base 44 to enhance conductions delivery to the tissue. For example, a conductive ink may have about 40-60% conductive silver particles with polyvinylchloride (PVC) particles with a solvent that evaporates to dry the ink on a surface of the electrode 12. Conductive plastic constructed of conductive particles and polymeric particles are fused together to form a conductive plastic.

Figure 5B:
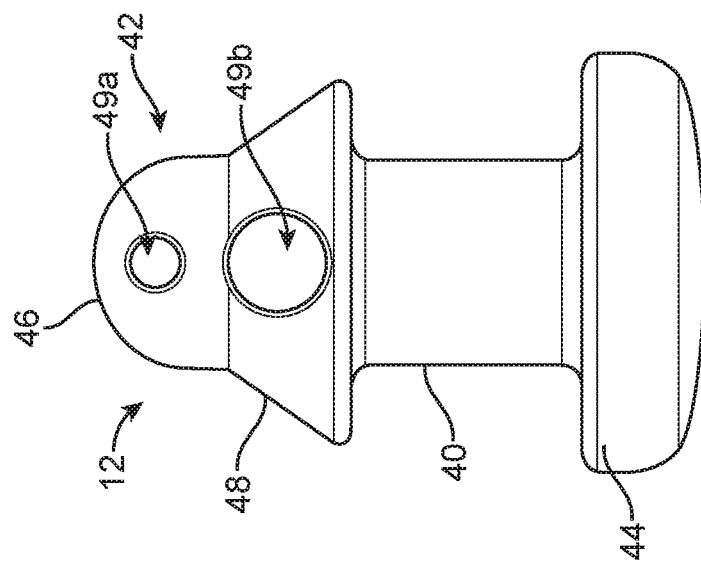
FIGS. 5A-5B illustrate the electrode of FIG. 4.
Figure 5A:
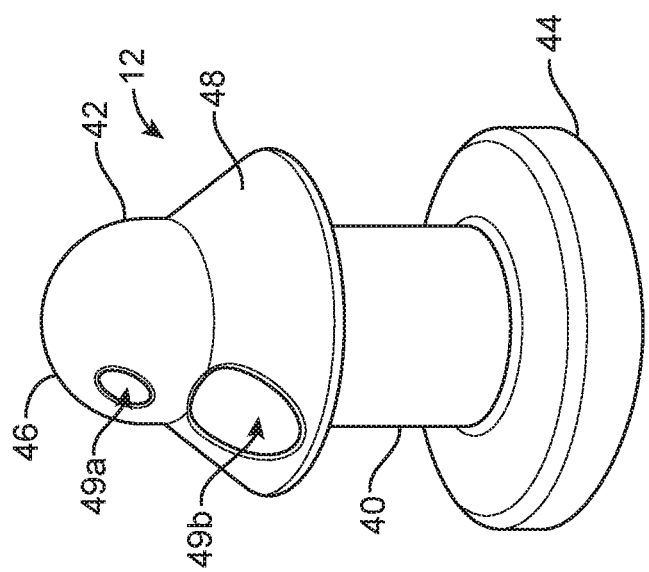

As best illustrated in FIGS. 4-5B, the electrode 12 can be configured to allow for crimping and strain relief of the lead wire assembly 60. The electrode 12 includes the axle 40, the top 42 and the base 44. Such features correspond with those of the channel 50 so that the electrode 12 is generally immovable with respect to the channel 50 Moreover, the top 42 can include a domed portion 46 interconnected to a flanged portion 48 extending outwardly with respect to the domed portion 46 and the axle 40. The top 42 includes first and second channels 49a, 49b, which are configured to retain portions of the lead wire assembly 60. In one embodiment, the first channel 49a is positioned within the domed portion 46 and can be crimped to the exposed wire core 66 proximate the top 42 using a single point crimp. The second channel 49b can be used to provide strain relief within the wire core 66 and can optionally be positioned to extend within the flanged portion 48. In certain embodiments, the top 42 is configured to provide a low profile wire core 66 interface. In the illustrated embodiment, the first channel 49a is configured to retain both the jacket 62 and the wire core 66 and the second channel 49b is configured to retain only the wire core 66. The electrode 12 can be made of an adhesive compatible material or can otherwise provide an adhesive compatible surface so that the wire core 66 can be secured to the top 42 of the electrode 12 with adhesive (not shown).

Although not shown, the electrode 12 can optionally be selectively electrically insulated. In such embodiments, the electrode 12 can be coated in an insulator completely (e.g., using chemical vapor deposition). This coating can then be selectively removed (e.g., using a laser) to expose desired areas. Alternatively, the electrode 12 can be masked and then an insulating coating can be applied.

The lead wire assembly 60 can optionally further include a sleeve 63 as is visible in FIG. 1. The sleeve 63 can be made of a material such as cotton or the like, which allows the clinician to stick the lead wire assembly 60 to a portion of a patient's anatomy (not shown). In such embodiments, the sleeve 63 can be optionally slidable along a length a of the jacket 62 so that the sleeve 63 can be selectively positioned at a portion along the jacket 62, wetted with water or the like, and then pressed onto the anatomy to facilitate adhesion of the sleeve 63 (and thus adhesion of the lead wire assembly 60) to the anatomy.

Figure 6A:
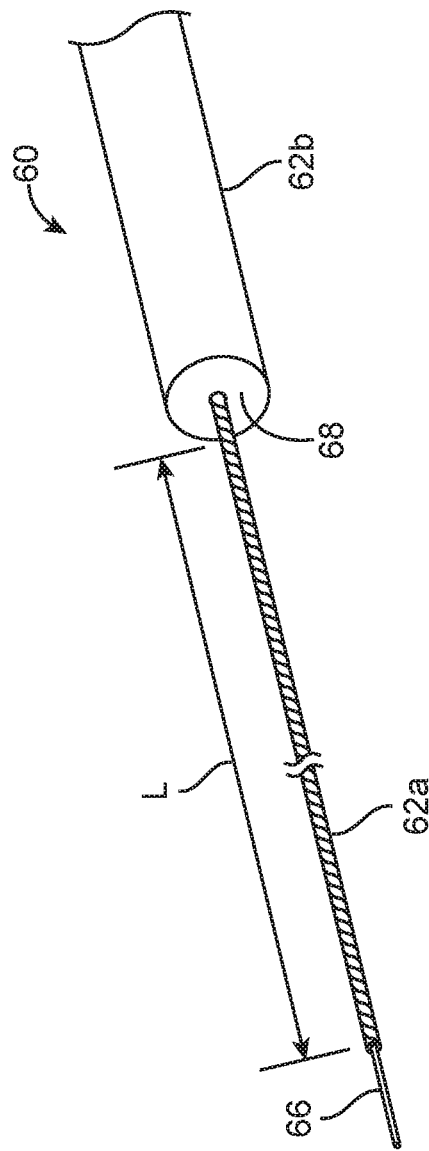
FIG. 6A is a perspective view of the lead wire assembly of FIGS. 1 and 4.
Figure 6B:
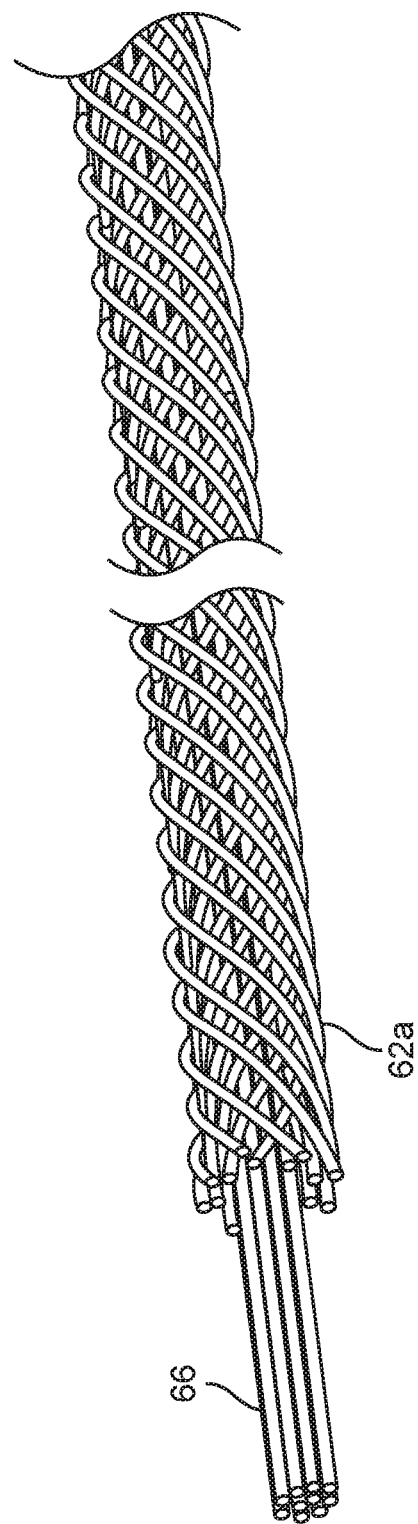
FIG. 6B is a partial, enlarged view of an inner jacket and wire core of the lead wire assembly of FIG. 6A.

Turning now also to FIGS. 6A-6B, which illustrate the lead wire assembly 60. The lead wire assembly 60 can include a single insulating jacket or can include both an inner jacket 62a and outer jacket 62b, which insulate the wire core 66. In embodiments where inner and outer jackets 62a, 62b are provided, the outer jacket 62b can be at least partially stripped from the inner jacket 62a to eliminate the need to potentially splice the lead wire assembly 60. In addition, a release agent 68 such as silicone or the like can be applied between the inner and outer jackets 62a, 62b to prevent adhesion between the inner and outer jackets 62a, 62b. In some embodiments, a length L of approximately 6 inches of the inner jacket 62a will be exposed with respect to the outer jacket 62b.

The lead wire assembly 60 is malleable and pliable having a thread-like flexibility while having a high-tensile strength. Where provided, the inner and outer jackets 62a, 62b (or single jacket) provides electrical insulation to the wire core 66 and, in some embodiments, is or are collectively thin to maintain flexibility of the lead wire assembly 60 or jacket(s) 62a/62b. In one example embodiment, the jacket or outer jacket 62b is made of a low-reflectivity material such as polyvinyl chloride (PVC) and provides electrical insulation of 1000VC dielectric strength. Where provided, the inner jacket 62a can be made of polytetrafluoroethylene (PTFE), for example. The wire core 66 is malleable to retain a deformed shape and can optionally be made of 300 series stainless steel 40AWG single strand material. The jacket(s) 62a, 62b can optionally be of a specific color, such as yellow to provide contrast with a patient's anatomy. As shown with respect to the lead wire assembly 60 in FIG. 7, the lead wire assembly 60 can further support electrical connections to the electrode 12 and/or APS system (not shown) via a pin jack 70 or the like that provides the electrical communication a patient interface (not shown). The pin jack 70 can be protected for International Electrotechnical Commission 60601 compliance.

Figure 7:
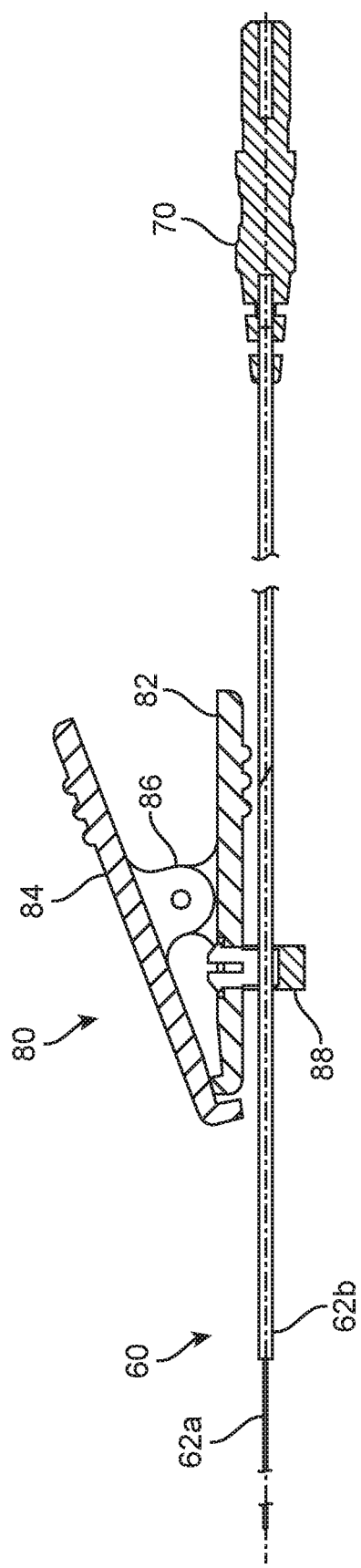
FIG. 7 is a cross-sectional view of a drape clip and a protected pin jack interconnected to the lead wire assembly such as that of FIGS. 6A-6B.

As generally illustrated in FIG. 7, a clip 80 can be secured to the lead wire assembly 60 to secure the lead wire assembly 60 to an ear/nose of the patient or, a sterile drape that covers the patient during surgery, for example, to provide strain relief within the lead wire assembly 60. The clip 80 can be configured to include two arms 82, 84 that include a hinged connection 86 biased in the closed position. The hinged connection 86 can include a pin about which the two arms 82, 84 can rotate. The two arms 82, 84 can be spring biased into the closed position. The clip 80 includes a mounting block 88 that secures one arm 82 to the jacket 22b. The mounting block 88 can be configured to allow the clip 80 to slide along a length of the lead wire assembly 60 with light resistance (e.g., 0.3 lbs. or less). In addition, the mounting block 88 can be connected to the clip 80 as to allow the clip 80 to rotate or spin 360 degrees with respect to the mounting block 88.

The cuff 14 can have a variety of configurations. An electrode assembly 110 having an alternate cuff 114 is shown in FIGS. 8-10. In this embodiment, the cuff 114 includes ears 122, 124 positioned on either side of a hinge segment 128, each ear 122, 124 having a respective foot 130, 132. In this embodiment, one ear 122 includes a channel 150 to maintain the electrode 12 and at least a portion of the lead wire assembly 60. Optionally, the channel 150 can include a conical lead in feature 156 for making it easier to thread the lead wire assembly 60 to the electrode 12. FIG. 9 illustrates the electrode assembly 110 achieving 360 degree dissection of a nerve N, whereas FIG. 10 illustrates the electrode assembly 110 achieving sub-360 degree (and greater than 180 degree) dissection of the nerve N. As will be apparent in view of this disclosure, the electrode assembly 110 can otherwise be identically configured and function identical to embodiments previously described.

Yet another embodiment of an electrode assembly 210 is illustrated in FIGS. 11A-11B. This electrode assembly 210 includes a cuff 214 having a body 216 defining a channel 220 and two ears or tabs 222, 224 extending radially outwardly from the body 216. As with prior embodiments, the ears 222, 224 are positioned on either side of a resilient hinge segment 238 that is configured and operates similar to previously described hinge segments. In some embodiments, one or more ears 222 can include a textured surface 226 including ridges or a foot 232, for example. In this embodiment, the two ears 222, 224 are not identically configured. In addition, a gap 236 formed by the body 216 of the cuff 214 is nonlinear and is generally wavy, which is beneficial for small diameter nerves that could potentially slip through the gap 236 if it were linear. Other non-linearly shaped gaps are envisioned. This electrode assembly 210 can be configured and function identically to those previously described in all other respects.

Figure 12A:
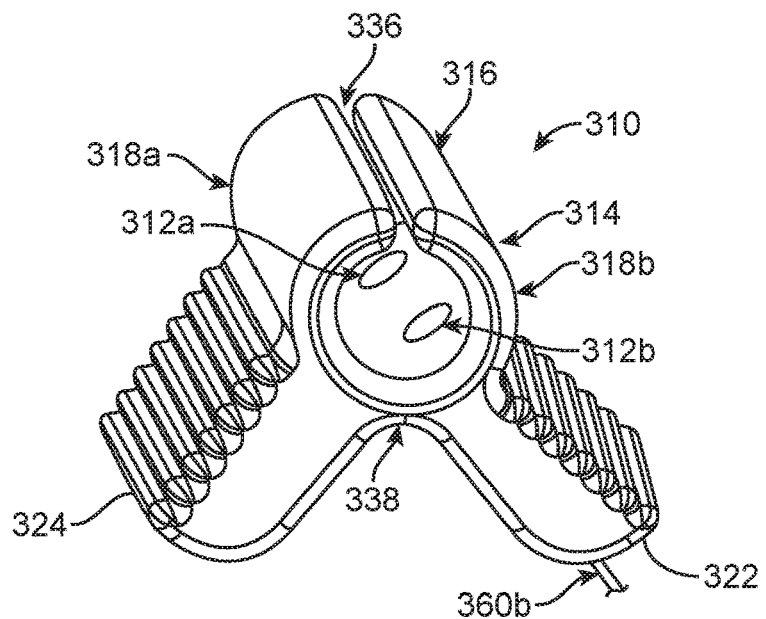
FIG. 12A is a perspective view of an alternate electrode assembly, which is substantially similar to embodiments previously illustrated but wherein the electrode assembly includes two electrodes.
Figure 12B:
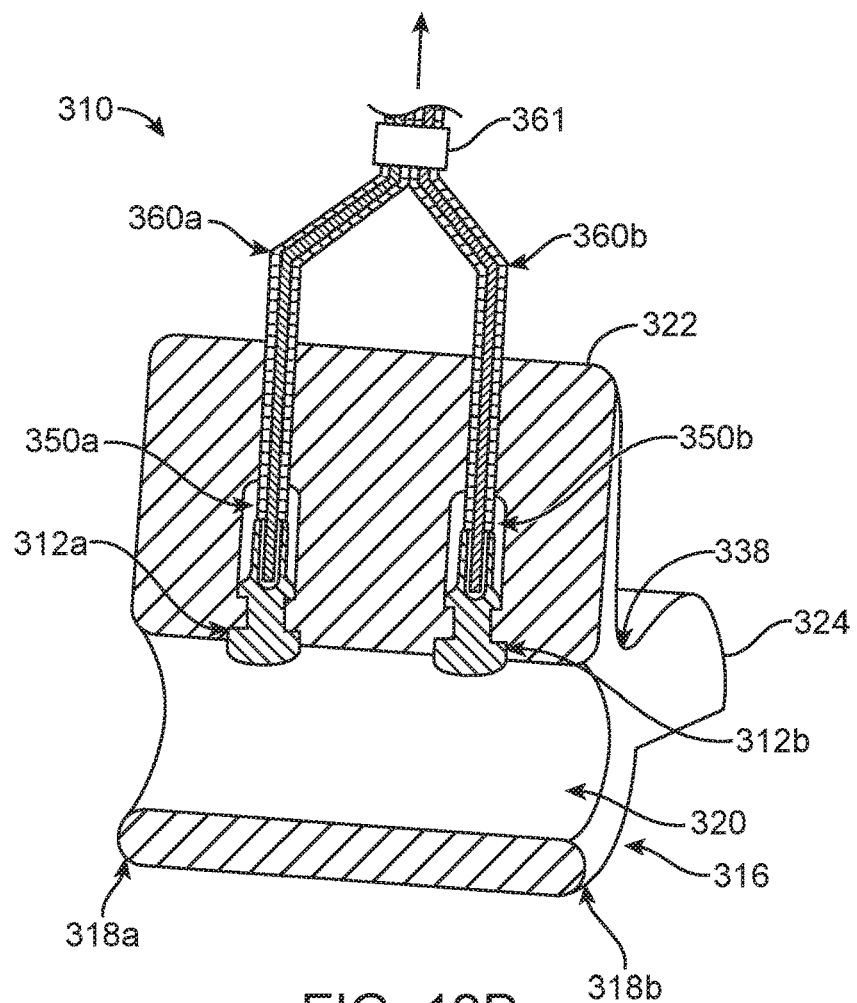
FIG. 12B is a cross-sectional view of the electrode assembly of FIG. 12B.

Yet another embodiment is illustrated in FIGS. 12A-12B. Electrode assembly 310 includes two electrodes 312a, 312b of the type previously disclosed, which are supported by and positioned within a cuff 314 including a body 316 having two parallel ends 318a, 318b. The body 316 further defines a channel 320 in which a nerve can be positioned. As shown, the body 316 can have a semi-circular cross-section (generally C-shaped) at both of the first and second ends 318a, 318b and/or throughout the body 316 along the channel 320. Extending radially from the body are two ears or tabs 322, 324. The ears 322, 324 can be configured as described with respect to prior embodiments. Similar to prior embodiments, the cuff 314 includes open and closed positions in which a width of a gap 336 formed by the body 316 and also the channel 320 of the body 316 are varied. The ears 322, 324 can be squeezed or moved together with the surgical instrument so that a resilient hinge segment 338 of the body 316 flexes and extends the width of the gap 336 and a diameter of the channel 320 (see also, FIGS. 3A-3B and related disclosure). Once the instrument releases the ears 322, 324, due to the resilient nature of the body 316, the cuff 314 transitions back to the position of FIG. 12.

The electrodes 312a, 312b, cuff 314 and the gap 336 can be as of the type described with respect to prior embodiments and are arranged and provide for continuous intraoperative monitoring and/or therapeutic stimulation in current and new procedures that place nerves at risk without extra dissection or necessarily wrapping of the electrode assembly 310 around substantially the entirety of the respective nerve. The electrode assembly 310 is configured for partially-dissected nerves in which at least about 50% or more of the circumference of the nerve is exposed. Although the electrode assembly 310 can be used will nerves that are fully dissected in which 100% of the circumference of the nerve is exposed, any level of dissection that is greater than about 50% of the circumference is suitable.

In this particular embodiment, the electrode assembly 310 is bipolar and includes first and second electrodes 312a, 312b spaced apart and supported within one or more channels 350a, 350b formed within one ear 322. The channels 350a, 350b can have a variety of configurations suitable for maintaining the position of the electrode(s) 312a, 312b. For example, each channel 350a, 350b can be configured as shown and described above with respect to the channel 50. Each electrode 312a, 312b is connected to a respective lead wire assembly 360a, 360b, which can each optionally be configured similar to the lead wire assembly 60 shown and described herein. The electrode assembly 310 can further optionally include one or more strain reducing features such as a clip assembly (see clip assembly 80 and related disclosure disclosed with respect to FIG. 7) and/or a band 361 that secures the two lead wire assemblies 360a, 360b together. As will be clear in view of the present disclosure, the electrode assembly 310 can be configured and function similar to other electrode assemblies disclosed above in all other respects not expressly addressed.

A self-retaining needle electrode assembly 410 is illustrated in FIGS. 13A-14B. The electrode assembly 410 includes first and second needle electrodes 412a, 412b; wherein the first needle electrode 412a includes a first tip 413a and the second needle 412b electrode includes a second tip 413b. The electrode assembly 410 further includes a body 416 having a first end 416a, a second end 416b, a first side portion 418a and a second side portion 418b. The body 416 interconnects the first and second needle electrodes 412a, 412b and includes a hinge segment 420 interconnecting the first and second side portions 418a, 418b as well as a first block 422a extending from the first portion 418a and a second block 422b extending from the second portion 418b.

Figure 13A:
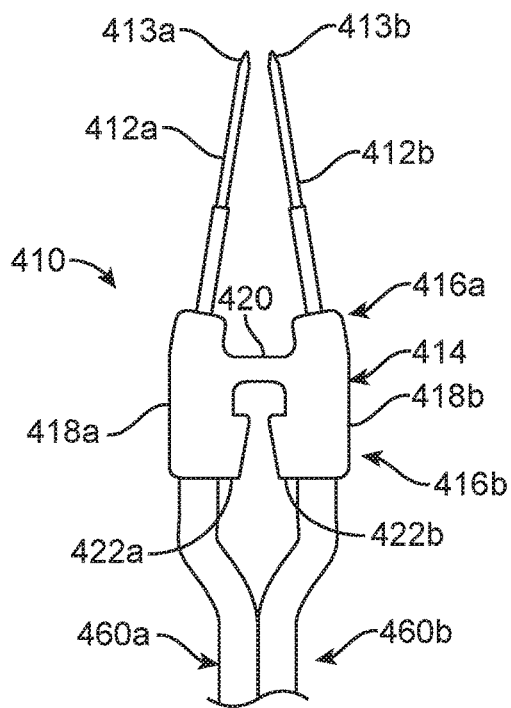
FIG. 13A is a plan view of a self-retaining needle electrode assembly in a natural arrangement.
Figure 13B:
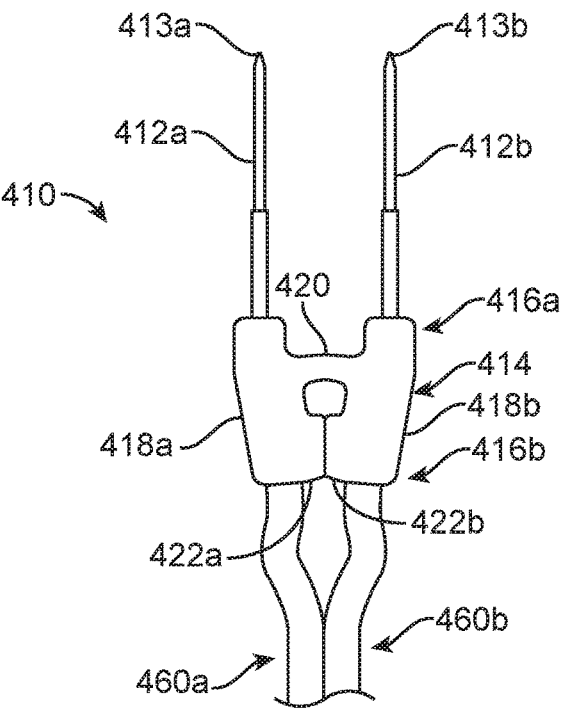
FIG. 13B is a plan view of the self-retaining needle electrode assembly in an expanded arrangement.
Figure 14A:
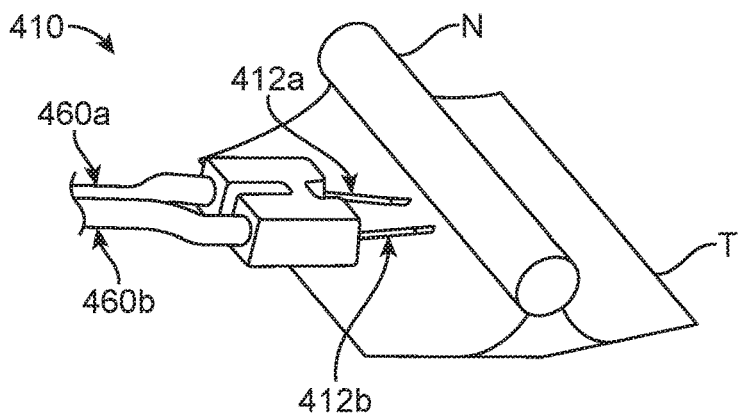
FIG. 14A is a perspective view of the self-retaining needle electrode assembly of FIGS. 13A-13B dissecting tissue proximate a nerve.
Figure 14B:
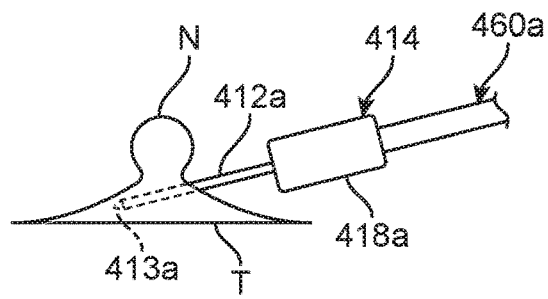
FIG. 14B is a side view of the self-retaining needle electrode assembly of FIG. 14A operatively positioned within tissue proximate a nerve.

As shown in FIG. 13A, the body 414 has a natural arrangement in which the first and second tips 413a, 413b are drawn toward one another and the first support block 422a is spaced from the second support block 422a. In various embodiments, the hinge segment 420 can be made of a resilient (elastomeric) material such as those suggested above with respect to the cuff 14, which allows the first and second portions 418a, 418b to move with respect to one another (e.g., FIG. 13B) while reverting back to the natural arrangement of FIG. 13A when a user has not applied external forces to the body 414. In the natural arrangement of FIG. 13A, the first portion 418a and the second portion 418b are positioned closer to one another at the first end 418a as compared to in an expanded arrangement of FIG. 13B. FIG. 13B illustrates the body 414 in the expanded arrangement in which the first and second side portions 418a, 418b are drawn together at the second end 416b such that the first and second tips 413a, 413b are positioned further away from each other as compared to the natural arrangement of FIG. 13A. In the expanded arrangement, the support blocks 422a, 422b can optionally be configured to touch one another and prevent over extension of the first and second tips 413a, 413b. As shown, the support blocks 422a, 422b can be positioned proximal with respect to the hinge segment 420. To use this electrode assembly 410, the first and second portions 418a, 418b are pressed toward each other at the second end 416b of the body 414 to increase the distance between the first and second tips 413a, 413b as is shown in FIG. 14B. Then, while in the expanded arrangement, the first and second needles 412a, 412b are inserted into tissue T proximate a nerve N (FIGS. 14A-14B). Then, the first and second portions 418a, 418b are released to allow the first and second tips 413a, 413b to move toward each other and into the natural arrangement of FIG. 13A, which engages the needle electrode assembly 410, within tissue T, proximate the nerve N for use. This embodiment is particularly useful when the nerve N is partially dissected (less than 100%, even less than 50%, of the circumference of the nerve N is exposed).

In the example embodiment illustrated, the electrode assembly 410 further includes lead wire assemblies 460a, 460b interconnected to each respective needle electrode 412a, 412b. As seen in a comparison of FIG. 13A to FIG. 13B, the first lead wire assembly 460a and the second lead wire assembly 460b are moveable with respect to one another proximate the second end 416b of the body 414. Each lead wire assembly 460a, 460b can optionally be connected to a clip 80 as is shown in and described with respect to FIG. 7 to provide strain relief. The needle electrode assembly 410 can be mono polar or can be biopolar configured. In a bi-polar configuration, each needle electrode 412a, 412b would be active and the lead wire assemblies 460a, 460b would now contain isolated conductors as would be understood by one of skill in the art.

Various electrode assemblies 10, 110, 210, 310 of the present disclosure can be delivered through a cannula inserted within a skin incision. In some embodiments, the cannula and skin incision are equal to or less than 5 mm. The electrode assemblies 10, 110, 210, 310, 410 are linked APS, for example, via one or more lead wire assemblies 60, 460a, 460b.

Although the present disclosure has been described with reference to preferred embodiments, workers skilled in the art will recognize that changes can be made in form and detail without departing from the spirit and scope of the present disclosure.

What is claimed is:

1. An electrode assembly for receiving a nerve; the electrode assembly comprising:
a cuff including a body having a first end, a second end, and defining a first channel configured to receive the nerve, the cuff further including first and second ears extending radially outwardly from the body; wherein a second channel is formed in the first ear; wherein, when in use the body further defines a nonlinear gap and a width of the gap is variable and configured to support a degree fixation of less than 360 degrees of a circumference of the nerve;
an electrode supported by and positioned within the second channel; and
a lead wire assembly interconnected to the electrode and extending within the second channel.

2. The electrode assembly of claim 1, further comprising a second electrode positioned within the cuff.

3. The electrode assembly of claim 1, wherein the second channel includes a conical lead-in feature.

4. The electrode assembly of claim 1, wherein the ears are interconnected by a hinge segment such that a distance between the first and second ears is variable.

5. The electrode assembly of claim 4, wherein the hinge segment is made of an elastomeric material.

6. The electrode assembly of claim 4, wherein varying the distance between the first and second ears correspondingly varies the width of the gap.

7. The electrode assembly of claim 1, wherein the gap is wavy.

8. The electrode assembly of claim 1, wherein the first and second ears are identically configured.

9. The electrode assembly of claim 1, wherein the first and second ears have a textured surface.

10. The electrode assembly of claim 1, wherein the first and second ears extend radially outwardly from the first channel.

11. The electrode assembly of claim 1, wherein the second channel has a first portion and a second portion, the electrode further including a base and an axle interconnecting the top and the base; wherein the first portion maintains the axle and the second portion receives the top.

12. The electrode assembly of claim 11, wherein the top has a domed portion and a flanged portion that extends outwardly with respect to the flanged portion.

13. The electrode assembly of claim 12, wherein the second portion includes an area of open space not occupied by the top.

14. The electrode assembly of claim 1, wherein the width of the gap is uniform.

15. The electrode assembly of claim 1, wherein the body has a semi-circular cross-section at both of the first and second ends.

16. An electrode assembly for receiving a nerve; the electrode assembly comprising:
a cuff including a body having a first end, a second end, and defining a first channel configured to receive the nerve, the cuff further including first and second ears extending radially outwardly from the body; wherein a second channel is formed in the first ear; wherein the body further defines a nonlinear gap and a width of the gap is variable and configured to support a degree fixation of less than 360 degrees of a circumference of the nerve;
an electrode supported by and positioned within the second channel; and
a lead wire assembly interconnected to the electrode and extending within the second channel;
wherein the second channel has a first portion and a second portion, the electrode further including a base and an axle interconnecting the top and the base; wherein the first portion maintains the axle and the second portion receives the top.

17. The electrode assembly of claim 16, wherein the top has a domed portion and a flanged portion that extends outwardly with respect to the flanged portion.

18. The electrode assembly of claim 17, wherein the second portion includes an area of open space not occupied by the top.

* * * * *